United States Patent [19]

Aronowitz et al.

[11] Patent Number: 4,877,580
[45] Date of Patent: Oct. 31, 1989

[54] ASSAY KIT INCLUDING AN ANALYTE TEST STRIP AND A COLOR COMPARATOR

[75] Inventors: Jack L. Aronowitz, Delray Beach; Louis Terminiello, Sunrise, both of Fla.

[73] Assignee: Technimed Corporation, Fort Lauderdale, Fla.

[21] Appl. No.: 153,967

[22] Filed: Feb. 9, 1988

[51] Int. Cl.⁴ .............................................. G01N 1/48
[52] U.S. Cl. ...................................... 422/58; 422/55; 422/56; 422/57; 422/61
[58] Field of Search .................................. 422/56–61, 422/86, 87; 435/14; 436/8–19

[56] References Cited

U.S. PATENT DOCUMENTS

| | | | |
|---|---|---|---|
| 2,370,683 | 3/1945 | Palma | 411/61 |
| 3,245,882 | 4/1966 | Guthrie | 422/56 |
| 3,891,507 | 6/1975 | Breuer | 422/58 |
| 4,056,359 | 11/1977 | Janin | 422/58 |
| 4,180,009 | 12/1979 | Voss et al. | 422/58 |
| 4,330,299 | 5/1982 | Cerami | 422/61 |
| 4,472,353 | 9/1984 | Moore | 422/56 |
| 4,486,536 | 12/1984 | Baker et al. | 422/61 |
| 4,663,126 | 5/1987 | Gould et al. | 422/61 |
| 4,772,560 | 9/1988 | Attar | 422/58 |
| 4,797,256 | 1/1989 | Watlington | 422/58 |

Primary Examiner—Barry S. Richman
Assistant Examiner—T. J. Wallen
Attorney, Agent, or Firm—John H. Faro

[57] ABSTRACT

An assay kit comprising an analyte test strip and a color comparator including a plurality of different color fields arranged in an ordered, preferably linear, succession. There is an aperture through each color field so positioned that the reaction zone of the test strip can be placed behind each color field and the color of the reaction zone thereafter viewed through each aperture, with the particular color field framing at least a portion of the reaction zone. The color comparator can be in the form of overlapping panels of a folder or a label on a bottle. There may be a chart of numerical assay values of the color fields such that the edge of the testing strip underlies the numerical value of the color field being viewed, or the testing strip may have a window therein which frames the numerical value of the color field being viewed. This invention has application in test kits for biological substances, (i.e. glucose, cholesterol) and drugs of abuse; and, in test kits for environmental toxins.

15 Claims, 1 Drawing Sheet

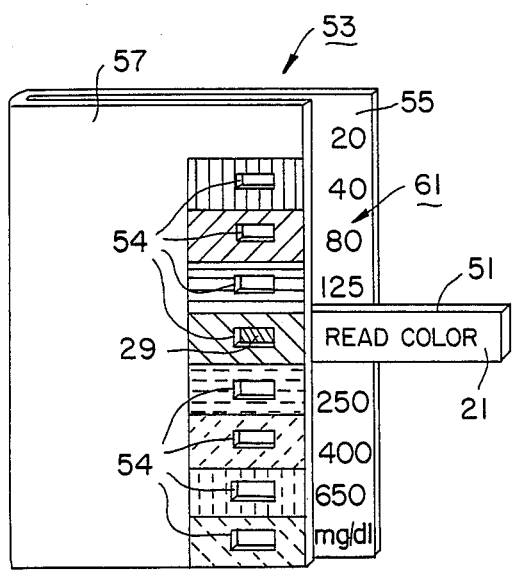
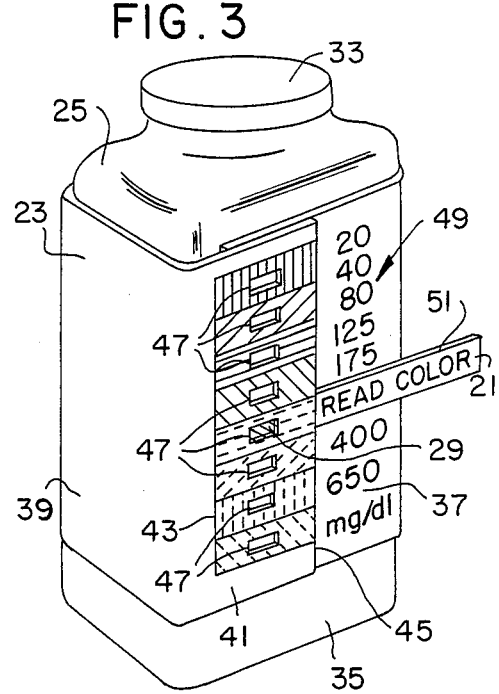
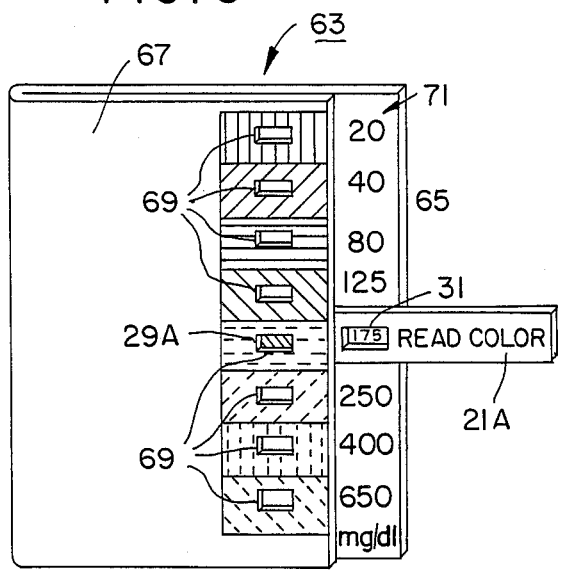
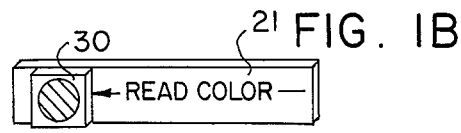
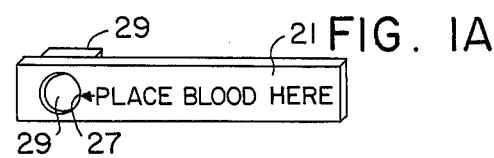
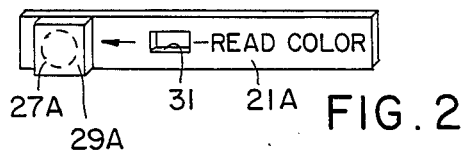

ASSAY KIT INCLUDING AN ANALYTE TEST STRIP AND A COLOR COMPARATOR

BACKGROUND OF THE INVENTION

1. Field of the Invention

This invention is directed to an article of manufacture and to a method. More specifically, this invention relates to a novel assay kit, particularly to a test kit employing an analyte test strip and a novel color comparator for the analyte. This kit includes a dry chemistry reagent system incorporated within a reaction zone of a bibulous medium (solid phase) of the test strip. The reagent system is specific for an analyte of interest. Such kits are useful in the detection of biological substances, i.e. glucose, cholesterol etc. and in the detection of environmental toxins.

2. Description of the Prior Art

Manual test kits are typically used for obtaining a qualitative or semi-quantitative assay value for an analyte, such as glucose, in a fluid sample. Representative test kits are available from the Ames division of Miles Laboratories (i.e. Bili-Labstix ®). One simple, low-cost, disposable kit can typically include a test strip having one or more reaction zones containing substances which produce a definitive set of color values in such zone in the presence of detectable quantitives of a particular analyte. The kit includes also a color comparator having a plurality of different color fields arranged in a linear succession for comparison with the color of the reaction zone. The color of each field connotes a particular assay value of the analyte.

In the Bili-Labstix ®, the test site is wetted with a urine sample. Then, after a designated period of time, each urine impregnated reaction zone within the test site of the test strip, is held over the color fields of the color comparator and the user tries to match the color of the reaction zone to the closest color among the color fields. In some of the more cumbersome of these test kits the user must refer to a separate numerical chart which translates the color fields into meaningful assay values.

One problem which arises when comparing and matching the reaction zone color with a color field is that the color of the support or inert portion of the analyte strip, (which is associated with the bibulous medium containing the analyte specific reactants), is usually white or near white. Because the inert portion of the strip is in the viewers visual field, it can change or distort the appearance of the color of the reaction zone to the naked eye. Also, in many such tests, the color of the reaction zone changes with time, so that the color must be matched promptly and the assay value obtained and recorded before a further color change prevents accurate correlation with the analyte content of the sample.

The following patents are representative of the prior art colorimetric assay test kits and techniques: U.S. Pat. Nos. 3,894,845 to B. McDonald; 3,964,974 to D. Banauch et al; 4,042,329 to H. T. Hochstrasser; 4,275,031 to W. Fischer et al; 4,391,904 to D. J. Litwan et al; and 4,532,216 to J. Y. Wang. As is evident from a review of these references, all the systems disclosed therein suffer from at least one common failing; the inability to permit rapid and accurate correlation of the reaction zone color with the appropriate comparative value in the companion color index.

OBJECTS OF THE INVENTION

Accordingly, it is the object of this invention to remedy the above as well as related deficiencies in the prior art.

More specifically, it is the principal object of this invention to provide an assay kit having an analyte strip and a unique color comparator.

A further object is to provide an assay kit in which the inert portions of the analyte strip are masked from the users field of view while the reaction zone color is being compared with the color fields of the color comparator.

Another object is to provide an assay kit which indicates the assay value of the color field that is matched to the color of the reaction zone of strip by the position of the analyte strip against the color comparator.

Still another object is to provide an assay kit having a color comparator that can be in the form of a folder or in the form of a label on a bottle.

SUMMARY OF THE INVENTION

The novel kit of this invention comprises an analyte testing strip having a localized region of reagents (hereinafter "reaction zone"), which produces a characteristic set of color values that correlate with the presence of specific assay values for a particular analyte, and a color comparator including a plurality of different color fields arranged in an ordered, preferably linear, succession, the color of each field connoting a particular assay value for said analyte.

Unlike prior assay kits, the color comparator of the novel kit has an aperture through each of the color fields thereof. There is also included a means permitting the reaction zone of the test strip to be placed closely behind each color field so that only the color of the reaction zone can be viewed through each aperture, with the particular color field framing the visible portion of the reaction zone. Upon such proper placement, the reaction zone is in an optimum position for color matching with each color field of the comparator without optical interference from other nearby colors which can affect or distort the appearance of the reaction zone to the naked eye.

The color comparator of the novel kit can be in the form of overlapping panels of a folder or as an extension of a label on a bottle. The analyte testing strip is slid into the space between the overlapping panels and positioned to view the patch through any of the apertures in the color comparator. The novel kit may have a chart of numerical assay values of the color field so positioned that the edge of the analyte testing strip underlines the numerical value of the particular field being viewed or, alternatively, the analyte testing strip may have a window therein which frames the numerical value of the particular field being viewed.

BRIEF DESCRIPTION OF THE DRAWINGS

FIG. 1A is a perspective view from above of a first analyte testing strip used in a preferred form of the novel kit.

FIG. 1B is a perspective view from below of the testing strip shown in FIG. 1A after sample has been applied and a reaction zone has been formed.

FIG. 2 is a perspective view of a second analyte testing strip used in an alternative form of the novel kit.

FIG. 3 is a perspective view of a first color comparator used in a preferred form of the novel kit.

FIG. 4 is a perspective view of a second color comparator used in a first alternative form of the novel kit.

FIG. 5 is a perspective view of the third color comparator used in a second alternative form of the novel kit.

DETAILED DESCRIPTION OF THE INVENTION INCLUDING THE PREFERRED EMBODIMENTS

The following description of some of the preferred embodiments of the concepts of this invention is made in reference to the accompanying figures. Where an individual structural element is depicted in more than one figure, it is assigned a common reference numeral for simplification of identification and understanding.

FIG. 1A illustrates a preferred analyte test strip (21) adapted to be used in combination with the label (23) on the bottle (25) shown in FIG. 3. This combination is used for the semiquantitative determination of glucose (the analyte) in whole blood. The test strip (21) comprises a disposable piece of heavy paper, light cardboard or plastic having an aperture (27) therein at one end thereof. A sample receptive pad (29) is attached to one side of the strip and completely covers the aperture (27). The aperture permits exposure of the reaction zone of the test strip to the sample absorbed on this pad. In typical operation, a whole blood sample is absorbed on the sample receptive pad, allowed to diffuse therein, whereupon it reconstitutes the reagents in the pad thereby initiating a colorimetric reaction which is manifest in the sample receptive pad of the test strip. The distribution of the sample within the pad defines a reaction zone (30). This pad can be a porous cellulose or plastic material impregnated with a dry chemistry reagent system specific for the analyte of interest. The aperture (27) forms a defined area, or well, on the obverse side of the strip (21) into which the sample, which is suspected of containing the analyte, is placed. FIG. 1A depicts the sample receptive side of the test strip bearing the inscription "PLACE BLOOD HERE". Placement of the sample in the well results in its spreading throughout the porous medium containing the dry chemistry reagent system and producing a distinctive color according to its assay value. After a designated period of time, the color of a reaction zone (30) within the porous medium is monitored on the reverse side of the test strip (21), which bears the inscription "READ COLOR" and an arrow pointing to the reverse side of the reaction zone (30) as shown in FIG. 1B.

FIG. 2 illustrates an alternative test strip (21A) having an aperture (27A) therein and a sample receptive pad (29A) covering the aperture (27A). This alternative testing strip design is identical in construction to the preferred strip (21) except that the alternative strip design has a window (31) at about its center which provides a modified read-out as will be described below.

The bottle (25) shown in FIG. 3 has a screw cap (33B) and a flat side (35). The label (23) wraps completely around the bottle (25) with the proximal panel (37) adhered to the flat side (35), the intermediate panels (37) attached to the other sides (39) of the bottle and the distal panel (41) overlapping the proximal panel but only tackified at its top and bottom, leaving a nonadhered space between the proximal and distal panels (37) and (41).

The distal panel (41) has an integral color comparator (43) including eight different color fields arranged in linear succession along the distal edge (45) of the distal panel (41). Each of the color fields has a centrally-located aperture (47) positioned so that it is framed by the color field. The aperture is smaller than the corresponding area of the reaction zone on the test strip, thereby insuring proper masking of distracting colors which border the reaction zone. In order to compare the color of the reaction zone (29) shown in FIG. 1, the strip (21) is slipped between the proximal and distal panels (37) and (41) with the reverse side of the patch (29) showing through an aperture, as shown in FIG. 3.

The proximal panel (37) has a scale (49) of numerical values corresponding to the assay values of each color field. The numerical values of the scale (49) are so offset and positioned that the upper edge (51) of the strip (21) underlines the numerical value of the field which corresponds to the color field surrounding the reaction zone (29). As shown in FIG. 3, the upper edge (51) of the strip (21) underlines the value "175" mg/dl glucose when the patch (29) is in the indicated aperture (47).

Instead of the color comparator being incorporated in an overlapping label as shown in FIG. 3, the color comparator can be incorporated into a pamphlet or folder (53) having a back panel (55) and an overlapping front panel (57). The color comparator is otherwise similar in construction to the color comparator shown in FIG. 3. The front panel (57) has eight color fields of different color values, each field having a centrally-located aperture (59) therein. The back panel (55) has a scale of numerical values (61), so positioned that the value of the reverse side of the reaction zone (29) is underlined by the edge (51) of the strip (21). As shown in FIG. 3, the value "125" mg/dl is glucose underlined when the reaction zone (29) is viewed through the appropriate window.

FIG. 5 shows an alternative color comparator incorporated into a pamphlet or folder (63) having a back panel (65) and an overlapping front panel (67). The front panel has eight color fields of different color values, each field having a centrally-located aperture (69) therein. The back panel (65) has a scale of numerical values (71), so positioned that the value of each color field is opposite the aperture (69) of that color field. The testing strip (21A) shown in FIG. 2 is used with this color comparator. As shown in FIG. 5, when the reaction zone (29A) is viewed through an aperture (69) in the color comparator, the corresponding numerical value is framed in the window (31) of the alternative testing strip (21A). As shown in FIG. 5, the value "175" mg/dl glucose is framed in the window (31).

The foregoing figures and descriptions thereof are provided as illustrative of some of the preferred embodiments of the concepts of this invention. While these embodiments represent what is regarded as the best modes for practicing this invention, they are not intended as delineating the scope of the invention, which is set forth in the following claims.

What is claimed is:

1. A test means comprising:
  (a) a test strip which includes an inert support and a sample receptive medium comprising a dry chemistry reagent system specific for an analyte of interest which upon interaction with said analyte produces a characteristic color indicative of an assay value of said analyte of interest, said receptive medium being positioned on said test strip so as to be bordered on one or more sides by said inert support;

(b) a color comparator including a plurality of different color fields representing a range of assay values of said analyte physically arranged in a predetermined ordered succession for comparison with the color of the sample receptive medium of the test strip, each of said color fields having an aperture which permits viewing therethrough of at least a portion of a reaction zone of the sample receptive medium after said analyte has reacted to produce a color therein, and (c) means for positioning said test strip relative to the aperture of each of said color fields so as to mask from view the inert support which borders the reaction zone of the sample receptive medium.

2. The test means defined in claim 1, wherein said color fields are on a folder of sheet material including a back panel and a closely-spaced front panel, and said means for positioning said test strip include said closely spaced front and back panels of said sheet material and adhesive-free space therebetween.

3. The test means defined in claim 1, including a container having a flat side and a label wrapped around and adhered to the outside surface of said container, said label having an overlapping panel on one side thereof, and wherein said color fields are on said overlapping panel and the means for positioning the test strip includes said overlapping panel, the overlapped portion of said label and adhesive-free space therebetween.

4. The test means defined in claim 1, including a numerical scale printed adjacent said color fields in a position such that said test strip identifies the numerical assay value of each color field when sample receptive medium is viewed through each said aperture.

5. The test means defined in claim 4, wherein the assay values are upwardly offset from their respective color fields such that an edge of said test strip underlines the correct assay value in said scale when the color of said reaction zone is viewed through each of said apertures.

6. The test means defined in claim 4, wherein said assay values are opposite their respective color fields, and said test strip has a window therein so positioned that the correct assay value in said scale is framed by said window when the color of said reaction zone is viewed through each of said apertures.

7. The test means defined in claim 1, wherein said analyte is glucose or cholesterol.

8. A test means comprising an analyte test strip having an analyte reaction zone and a color comparator therefor, said color comparator comprising a plurality of color fields physically arranged in a linear succession, each successive field connoting a different numerical assay value of said analyte, characterized in that each color field has an aperture therethrough entirely framed by said color field, each aperture permitting at least a portion of said reaction zone to be viewed when said reaction zone is positioned behind the color field framing that aperture.

9. The test means defined in claim 8, wherein said test strip includes a bibulous sample receptive medium attached to said strip near one end thereof, said medium containing a dry chemistry reagent system which produce a definitive set of colors in said medium in the presence of detectable quantities of a particular analyte.

10. The test means defined in claim 9, wherein said color comparator includes a back panel of sheet material and an overlapping front panel closely spaced from said back panel, said front panel having a distal edge and carrying said color fields along said distal edge thereof, said test strip being adapted to be slid between said panels into positions whereby said reaction zone can be framed by said apertures.

11. The test means defined in claim 10, including a scale of numerical values corresponding to said color fields and located on said back panel in such positions that each value is identified by said strip when said reaction zone is viewable through each said aperture.

12. The test means defined in claim 11, wherein said numerical value is underlined by the edge of said strip.

13. The test means defined in claim 11, wherein said numerical value is framed by a window in said strip.

14. A test means comprising:

(a) test strip which includes an inert support and a sample receptive medium comprising a dry chemistry reagent system specific for an analyte of interest which upon interaction with said analyte produces a characteristic color indicative of an assay value of said analyte of interest, said receptive medium being positioned on said test strip so as to be bordered on one or more sides by said inert support;

(b) a color comparator comprising a folder having a back panel, a closely-spaced front panel, and an adhesive-free space therebetween, said front panel, including a plurality of different color fields representing a range of assay values physically arranged in a predetermined ordered succession for comparison with the color of the sample receptive medium of the test strip, each successive field connoting a different numerical assay value, each of said color fields having an aperture which permits viewing therethrough of at least a portion of a reaction zone of the sample receptive medium after said analyte has reacted to produce a color therein; and (c) means for positioning said test strip between said front panel and said back panel and relative to the aperture of each of said color fields so as to mask from view the inert support which borders the reaction zone of the sample receptive medium.

15. A test means comprising:

(a) a test strip which includes an inert support and a sample receptive medium comprising a dry chemistry reagent system specific for an analyte of interest which upon interaction with said analyte produces a characteristic color indicative of an assay value of said analyte of interest, said receptive medium being positioned on said test strip so as to be bordered on one or more sides by said inert support;

(b) a container and a label wrapped around and adhered to the outside surface of said container, said label having a distal panel on one side thereof overlapping a proximal panel on the other side thereof, and an adhesive-free space therebetween, (c) a color comparator, comprising said overlapping distal panel and said overlapped proximal panel, said overlapping distal panel including a plurality of different color fields representing a range of assay values physically arranged in a predetermined ordered succession for comparison with the color of the sample receptive medium of the test strip, each successive field connoting a different numerical assay value, each of said color fields having an aperture which permits viewing therethrough of at least a portion of a reaction zone of the sample receptive medium after said analyte has reacted to produce a color therein; and (d) means for positioning said test strip between said distal panel and said proximal panel and relative to the aperture of each of said color fields so as to mask from view the inert support which borders the reaction zone of the sample receptive medium.

* * * * *